United States Patent [19]

Kiyota et al.

[11] Patent Number: 5,204,327
[45] Date of Patent: Apr. 20, 1993

[54] TREATMENT OF CEREBRAL EDEMA WITH ANP PHARMACEUTICAL COMPOSITIONS

[75] Inventors: Takao Kiyota; Shuichi Sugawara; Hiroshi Hayashi, all of Shizuoka, Japan

[73] Assignee: Ashi Kasei Kogyo Kabushiki Kaisha, Japan

[21] Appl. No.: 435,659

[22] Filed: Nov. 13, 1989

[30] Foreign Application Priority Data

Nov. 18, 1988 [JP] Japan ................................ 63-290173

[51] Int. Cl.$^5$ ...................... A61K 37/02; C07K 7/10
[52] U.S. Cl. ......................................... 514/12; 514/11
[58] Field of Search ................................. 514/11, 12

[56] References Cited

U.S. PATENT DOCUMENTS

4,663,437  5/1987  de Bold ............................. 530/324

FOREIGN PATENT DOCUMENTS

60-136596  2/1985  Japan .

OTHER PUBLICATIONS

Doczi et al. Neurosurgery, vol. 21, #4, Oct. (1987) pp. 454–458.
Doczi et al. Acta Neurochirurgica, vol. 43, Supplement 43, 1980, pp. 186–458.
Klatzo, I., "Neuropathological aspects of brain edema," J. Neuropath, Exp. Neurol., 26, 1–14 (1967).
Fishman, R. A., "Brain edema," New England J. Med., 293, 706-(1975).
Marc Cantin and Jacques Genest, "The Heart as an Endocrine Gland," Scientific American, 254, 62–67 (1986).
Bianchi, C., et al., "Radiautographic Localization of $^{125}$I-Atrial Natriuretic Factor Binding Sites in the Brain," Neuroendocrinology, 44 365–372 (1986).
Steardo, L. and Nathanson, J. A., "Brain Barrier Tissues: End Organs for Atriopeptins," Science, 235, 470–473 (1987) p. 11.
Watanabe et al., Eur. J. Pharmacol., 147, 49–57 (1988).
Imai, T. et al., "Effect on ANP on kidney," Protein–Nucleic Acid–Enzyme, 113 (14), 2476–2489 (1988).

*Primary Examiner*—Lester L. Lee
*Attorney, Agent, or Firm*—Lowe, Price, LeBlanc & Becker

[57] ABSTRACT

A pharmaceutical composition and its use in the treatment of cerebral edema are provided wherein the composition comprises an atrial natriuretic peptide having an amino acid sequence of 28 amino acids and at least one pharmaceutically acceptable carrier, diluent or excipient.

7 Claims, 2 Drawing Sheets

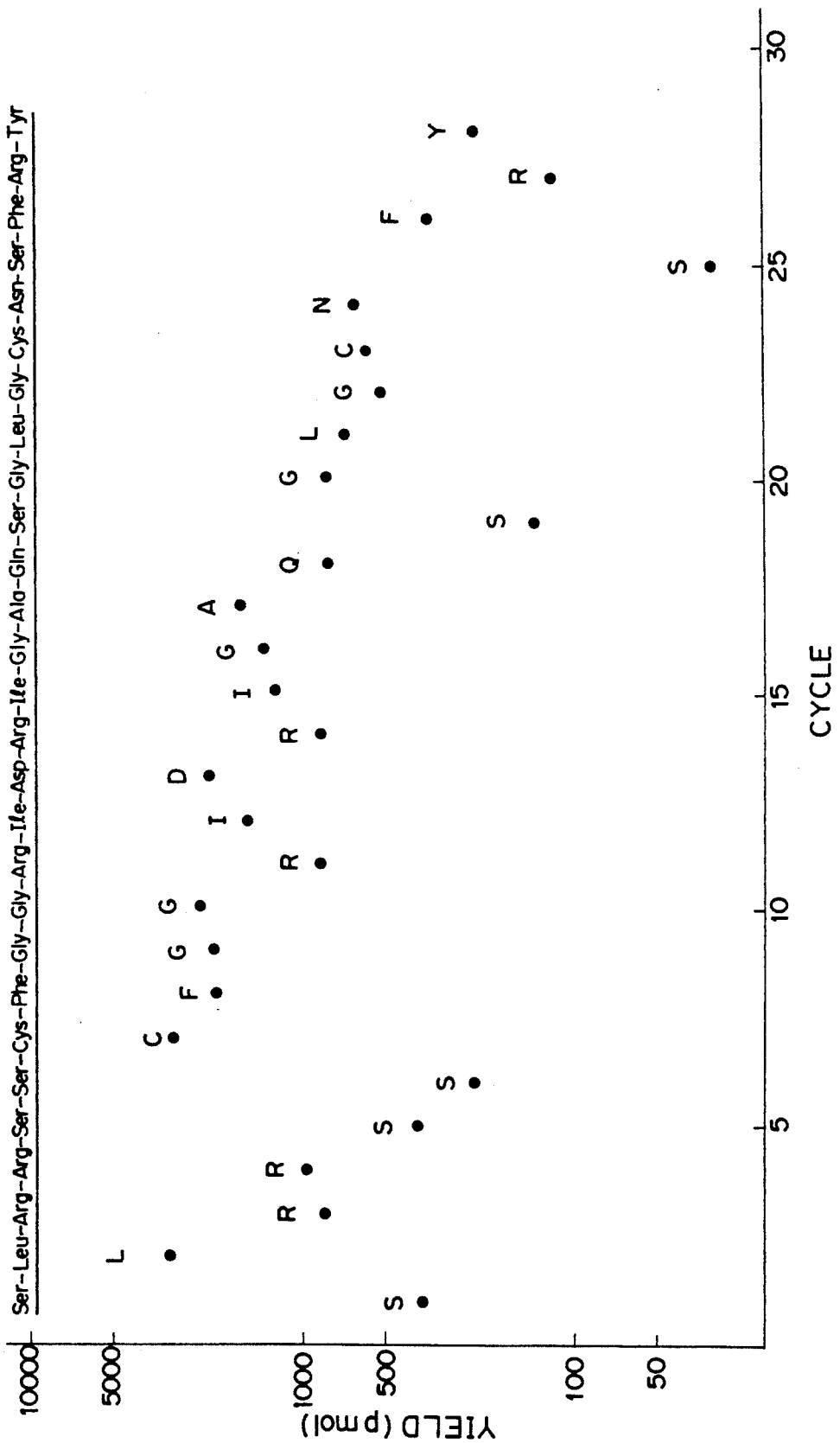

TREATMENT OF CEREBRAL EDEMA WITH ANP PHARMACEUTICAL COMPOSITIONS

BACKGROUND OF THE INVENTION

1. Field Of The Invention

This invention relates to a pharmaceutical composition for use in the treatment of cerebral edema. More particularly, the present invention relates to a pharmaceutical composition containing a peptide having anti-cerebral edema activity. The pharmaceutical composition of the present invention can advantageously be used not only as a medicine for the treatment of cerebral edema, but also as a medicine for the prevention of cerebral edema.

2. Discussion Of Related Art

Cerebral edema is a symptom defined as an excessive accumulation of water in a brain tissue, which is caused by various brain injuries. Cerebral edema accompanies an increase in intracranial pressure. In more serious cases, cerebral edema itself functions to increase the intracranial pressure. The mechanism of the occurrence of cerebral edema varies according to the type of brain injury. Klatzo defined two types of cerebral edemas. One type is vasogenic edema which is caused by the transfer of water into a brain tissue, which water is leaked out of a blood-brain barrier, simultaneously with the leakage of a serum protein from the blood-brain barrier due to the damage thereof. The other type is cytotoxic edema which is caused by the water retained in a brain tissue due to the inhibition of the transfer of ions between the inside and the outside of the cell membrane of a brain tissue, which inhibition accompanies the metabolic inhibition of a brain tissue cell [Klatzo, I., "Neuropathological aspects of brain edema", J. Neuropath. Exp. Neurol., 26, 1-14(1967)]. According to clinical observation, most of the cerebral edemas are vasogenic edemas, while cytotoxic edema accompanies limited types of diseases, such as cerebral ischemia at a primary stage thereof, water poisoning and meningitis purulenta. Further, Fishman reported another type of cerebral edema, that is, interstitial edema which is caused by the reservation of cerebrospinal fluid in a cerebral medulla surrounding the cerebral venticles, ascribed to hydrocephalus [Fishman, R.A., "Brain edema", New Eng. J. Med., 293, 706 (1975)].

Heretofore, with respect to the treatment of cerebral edema, it has generally been attempted to remove water from a brain tissue on one hand and block intracranial pressure-increasing factors on the other. In this attempt, a surgical method and a pharmaceutical method are employed. In the surgical method, water is removed from a brain tissue so that the intracranial pressure can be reduced. As the pharmaceutical method, there can be mentioned, for example, a method in which a hypertonic solution, such as a glycerol solution, is administered. In this method, excess water in a brain tissue and other tissues is drawn out into a blood, followed by excretion as urine by the osmotic diuresis action of the hypertonic solution. Further, a steroid therapy and a barbital therapy can be mentioned as a therapeutic method for the treatment of cerebral edema. In the steroid therapy, a steroid is administered in a large amount in a short period so as to suppress the symptoms of cerebral edema. In the barbital method, barbital is administered for controlling the metabolism of a brain to thereby relieve the symptom. The administration of barbital is also effective to capture free radicals accumulated in the blood-brain barrier, which free radicals are likely to cause vasogenic edema, one type of cerebral edema, to thereby remove the cause of cerebral edema.

However, the above-mentioned conventional methods have various disadvantages. For example, the hypertonic solution method is disadvantageous in that the administration of a hypertonic solution for a long time causes abnormal homeostasis of water and electrolyte and there is a danger that when the administration is suspended, the intracranial pressure is temporarily increased as rebound phenomenon. Further, the steroid method is disadvantageous in that it has side effects, for example, hemorrhage in the digestive tract, susceptibility to infection, carbohydrate metabolic inhibition and the like. Moreover, the barbital method is disadvantageous in that the management of respiration of a patient at the time of the administration of barbital is difficult and that the hepatic insufficiency is likely to be caused when barbital is administered in a large amount.

On the other hand, in recent years, studies on atrial natriuretic peptide (hereinafter referred to as "ANP") which is a peptide derived from an atrium have been progressed, and various studies on the application of ANP have been made.

For example, a diuretic and an antihypertensive agent using ANP have been developed (Japanese Patent Application Laid-Open Specification No. 60-136596).

Further, Marc Cantin et al. determined the relationship between ANP and cyclic guanosine monophosphate (GMP), which acts as a messenger for the control of water content. They also found that ANP is capable of binding to various portions of the ciliary body of eyes. This fact suggests that ANP has a relation with the control of intraocular pressure and it can be used for treating a glaucoma [Marc Cantin and Jacques Genest, "The Heart as an Endocrine Gland", Scientific American, 254, 62-67 (1986)]. Thereafter, it has been attempted to develop a pharmaceutical composition for the treatment of glaucoma, containing ANP as an active ingredient.

Furthermore, Marc Cantin et al. administered $^{125}$I-ANP to a rat through a carotid artery and examined the brain of the rat by radioautography. As a result, it was found that $^{125}$I-ANP-binding site is present in the epithelial cells of the choroid plexus of each of the third cerebral venticle, the fourth cerebral venticle and the lateral venticle. At that time, it was already known that a cerebrospinal fluid is produced mainly in the choroid plexus. Based on these findings, they suggested that ANP controls the production of a cerebrospinal fluid [Bianchi, C., Gutkowska, J., Ballak, M., Thibault, G., Garcia, R., Genest, G., Cantin M., "Radioautographic Localization of $^{125}$I-Atrial Natriuretic Factor Biding Sites in the Brain", Neuro-endocrinology, 44, 365-372(1986)].

Further, Nathanson et al. found that when ANP is added to the epithelial cells of the choroid plexus isolated from a rabbit, which cells are capable of producing a cerebrospinal fluid, the amount of an intracellular cyclic GMP is increased. From this finding, they considered that the epithelium of the choroid plexus is a target organ of ANP and the ANP affects the secretory function of the epithelial cells. They also found that the intraventicular administration of ANP is effective for inhibiting the production of a cerebrospinal fluid. Thus, they substantiated the hypothesis of Marc Cantin et al. with respect to the activity of ANP for controlling the cerebrospinal fluid production. From these findings, they suggested that ANP can be used for treating hydrocephalus which is caused by the insufficiencies of the cerebrospinal fluid circulation system [Steardo, L., and Nathanson, J.A., "Brain Barrier Tissues: End Organs for Atriopeptins", Science, 235, 470–473(1987)].

As described above, the activity of ANP for controlling the cerebrospinal fluid production has already been known and the effectiveness of the use of ANP for the treatment of glaucoma, hydrocephalus, etc. has been suggested. However, it has not yet been suggested that ANP is effective for relieving the symptom of cerebral edema which is caused by various mechanisms.

SUMMARY OF THE INVENTION

The present inventors have made extensive and intensive studies with respect to the pharmaceutical activities of ANP. As a result, it has been found that ANP is effective for controlling the accumulation of water in the brain of an established animal model having cerebral edema, which model is recognized in the art to be most reliable of examining the anti-cerebral edema activity of a certain substance, that is, it has for the first time been found that ANP exhibits excellent anti-cerebral edema activity. Based on the above finding, the present invention has been completed.

Accordingly, it is an object of the present invention to provide a pharmaceutical composition which is effective for treating cerebral edema.

The foregoing and other objects, features and advantages of the present invention will be apparent to those skilled in the art from the following detailed description taken in connection with the accompanying drawings.

BRIEF DESCRIPTION OF THE DRAWINGS

FIG. 2 shows the results of amino acid sequence analysis of the peptide synthesized in Reference Example 1 as is described later.

DETAILED DESCRIPTION OF THE INVENTION

Figure 1:
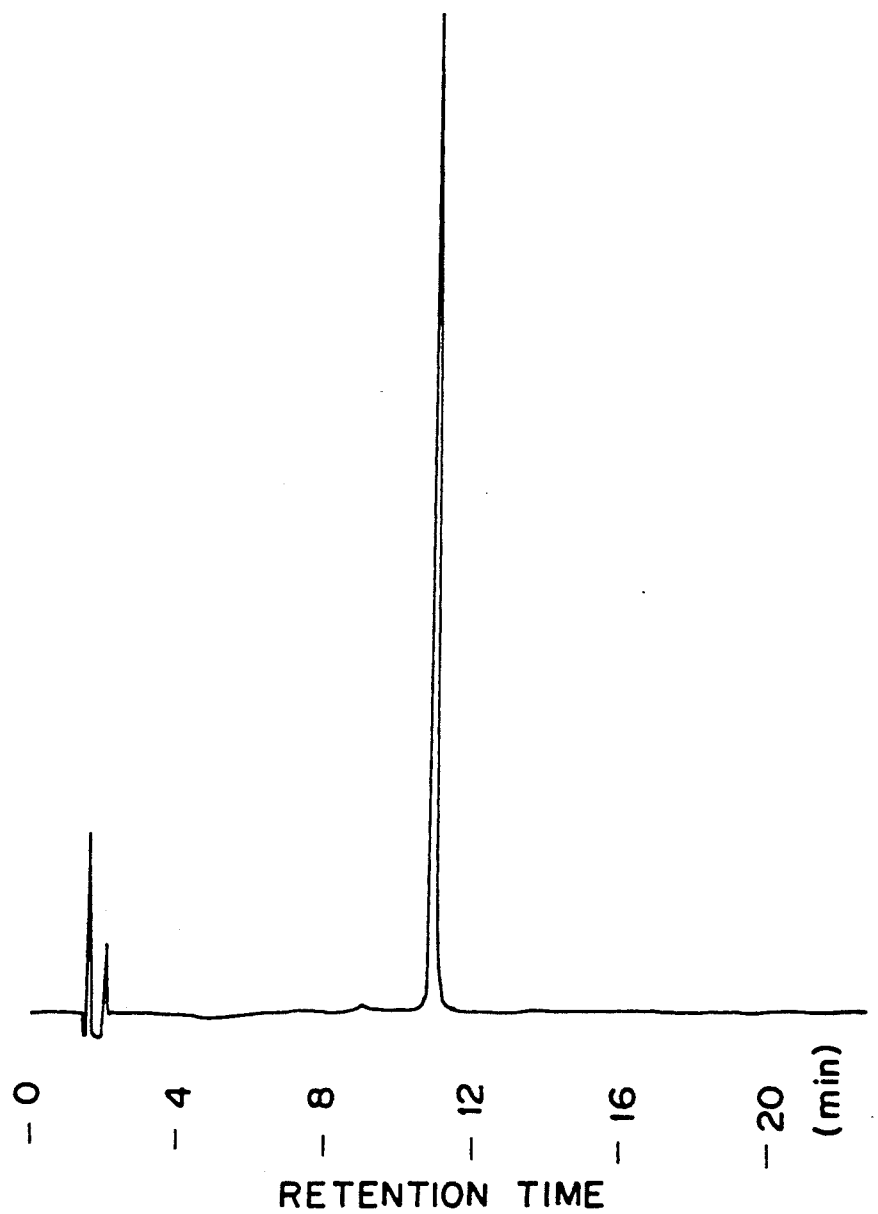
FIG. 1 shows a high-performance liquid chromatogram of the peptide synthesized in Reference Example 1 as is described later.

According to the present invention, there is provided a pharmaceutical composition for the treatment of cerebral edema, comprising an effective anti-cerebral edema amount of at least one peptide represented by formula (I):

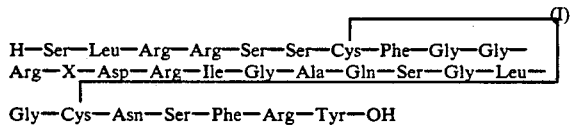

wherein X is an isoleucine residue or a methionine residue,
and at least one pharmaceutically acceptable carrier, diluent or excipient.

The pharmaceutical composition of the present invention contains as an active ingredient at least one peptide represented by formula (I) described above which is known as ANP. That is, the composition contains at least one of the peptides represented by formulae (II) and (III):

```
              ┌─────────────────────(II)
H—Ser—Leu—Arg—Arg—Ser—Ser—Cys—Phe—Gly—Gly—
Arg—Ile—Asp—Arg—Ile—Gly—Ala—Gln—Ser—Gly—Leu—
     ┌─
Gly—Cys—Asn—Ser—Phe—Arg—Tyr—OH,
``` and

```
              ┌─────────────────────(III)
H—Ser—Ile—Arg—Arg—Ser—Ser—Cys—Phe—Gly—Gly—
Arg—Met—Asp—Arg—Ile—Gly—Ala—Gln—Ser—Gly—Leu—
     ┌─
Gly—Cys—Asn—Ser—Phe—Arg—Tyr—OH,
``` wherein Ser represents a serine residue, Leu a leucine residue, Arg an arginine residue, Cys a cysteine residue, Phe a phenylalanine residue, Gly a glycine residue, Ile an isoleucine residue, Asp an aspartic acid residue, Ala an alanine residue, Gln a glutamine residue, Asn an asparagine reside and Tyr a tyrosine residue.

Of peptides (II) and (III), peptide (II) is more preferred since peptide (II) has relatively high anti-cerebral edema activity as compared to peptide (III).

In the present invention, any homologous variants of the peptide described above also may be used as an active ingredient, as long as the homologous variants have similar physiological activities. For example, deletion of the N-terminal amino acid Ser in formula (I) does not affect the physiological activities, such as chick rectum-relaxing activity, rat aorta-relaxing activity and Na-diuretic activity. However, the C-terminal amino acid sequence of the peptide is important because the aorta-relaxing activity and Na-diuretic activity are adversely affected when two amino acids Arg and Tyr are removed from the C-terminal of the peptide of formula (I). Further, the circular structure formed by the disulfide bond between two cysteines (Cys) in formula (I) is important for the physiological activities [Protein-Nucleic Acid-Enzyme, 113(14), 2476–2489(1988), and Watanabe et al., Eur. J. Pharmacol., 147, 49–57(1988)].

The amino acids constituting the peptide to be used in the present invention may be either of the L-configuration or of the D-configuration.

The peptide to be used in the present invention may be in free form. The peptide may also be in the form of a salt as long as the salt is pharmaceutically acceptable. Examples of salts include metal salts, such as sodium salt, potassium salt, lithium salt and calcium salt; salts with organic bases; salts with inorganic acids, such as sulfuric acid, hydrochloric acid and phosphoric acid; and salts with organic acids, such as acetic acid and maleic acid.

The peptide of formula (I) may be prepared by a customary technique for the peptide synthesis or by recombinant DNA technique described, for example, in the following references:

(1) Seikagaku Jikken Koza (Lectures on Experiments in Biochemistry) 1, "Tanpakuskitsu-no-kagaku (Protein chemistry) IV", written by Haruaki Yajima and Shunpei Sakakibara, edited by Japanese Society of Biochemistry, published by Tokyo Kagaku Dojin K.K., pp.207–495(1977), (2) Peputido Gosei (Peptide Synthesis), written by Nobuo Izumiya et al., published by Maruzen K.K., Japan (1980);

(3) Zoku-Seikagaku Jikken Koza (Lectures on Experiments in Biochemistry, Second series) 2, Tanpakushitsu-no-Kagaku (Protein Chemistry), the last volume, written by Toshi Kimura et al., published by Tokyo Kagaku Dojin K.K, pp. 641-694 (1987);

(4) Peputido Gosei-no-Kiso to Jikken (Fundamentals and Experiments of Peptide Synthesis), written by Nobuo Izumiya et al., published by Maruzen K.K., Japan (1985), and (5) Molecular Cloning, A Laboratory Manual, written by T. Maniatis et al., published by Cold Spring Harbor Laboratory, Cold Spring Harbor, New York (1982).

Generally, the peptide of formula (I) may advantageously be produced by the solid phase method of Merrifield et al., or by the liquid phase method. In each method, when amino acids have amino group and carboxyl group which will not participate in forming a peptide bond, and other functional groups, such as a hydroxyl group and a guanidyl group, part or all of these functional groups may advantageously be protected by protective groups customarily used for the peptide synthesis, according to a conventional method. After the synthesis of the peptide, the protective groups are removed by a conventional method, for example, by the treatment with hydrogen fluoride or trimethylsilyl-trifluoromethanesulfonate. Then, the resultant peptide is oxidized to form a disulfide bond between the thiol groups of two cysteine residues present in the peptide. The resultant peptide may be purified by using the conventional techniques, such as ion exchange column chromatography, gel filtration column chromatography, hydrophobic chromatography and reverse phase high-performance liquid chromatography, individually or in combination. Thus, the peptide of formula (I) can be obtained in substantially pure form.

The peptide or a pharmaceutically acceptable salt thereof is blended with at least one pharmaceutically acceptable carrier, diluent or excipient.

Suitable carriers, diluents and excipients include albumin, globulin, methylcellulose, purified gelatin, gelatin, polyethylene glycol, sucrose, D-sorbitol, protamine, glucose, galactose, xylose, fructose, maltose, glycerol mannitol, glucuronic acid, trehalose, dextran, hydroxyethyl startch, citric acid, sodium citrate, sodium hydrogen citrate, tartaric acid, acetic acid, sodium acetate, lactic acid, L-phenylalanine, L-histidine hydrochloride, L-glutamic acid, phenylalanine, alanine, sodium chloride, sodium dihydrogenphosphate, disodium hydrogenphosphate, sodium hydrogencarbonate, and nonionic surfactants, such as a polyoxyethylene fatty acid ester, a polyoxyethylene alkyl ether, a polyoxyethylene alkyl phenyl ether, a polyoxyethylene sorbitan fatty acid ester, a polyoxyethylene glycerin fatty acid ester, a polyoxyethylene hardened castor oil, a polyoxyethylene castor oil, a polyoxyethylene-polyoxypropylene alkyl ether a polyoxyethylene-polyoxypropylene block copolymer, a sorbitan fatty acid ester, a sucrose fatty acid ester and a glycerin fatty acid.

The pharmaceutical composition of the present invention can be formulated into various preparations adapted, for example, to intravenous, intramuscular and subcutaneous injections and oral administration. The peptide of formula (I) per se is likely to be degraded in the digestive tract. Therefore, when oral administration is intended with respect to the pharmaceutical composition of the present invention, it is preferred that a pharmaceutical composition be in a form such that the peptide contained in the composition is unlikely to be degraded, for example, be in the form of a microcapsule comprising a liposome and the peptide encapsulated therein. Further, the pharmaceutical composition of the present invention may also be formulated into preparations adapted to administration to mucous membranes other than that of the digestive tract, such as a rectal mucous membrane, an intranasal mucous membrane and a sublingual mucous membrane. Representative examples of such preparations are a suppository, a nasal drop and a sublingual tablet. Of the above-mentioned preparations, preferred are preparations adapted to intravenous, intramuscular and subcutaneous administrations.

In another aspect, the present invention provides a method for treating cerebral edema, which comprises administering to a patient having cerebral edema an effective anti-cerebral edema amount of at least one peptide represented by formula (I).

The peptide may generally be administered in the form of a pharmaceutical composition described above. The dose of the peptide may be varied according to the type of cerebral edema, the age and weight of a patient, the symptom and the method of the administration. Generally, the peptide can be administered to a cerebral edema patient in an amount of from 0.1 $\mu$g to 10 mg/kg-weight of a patient per dosage, preferably from 1 $\mu$g to 1 mg/kg-weight of a patient per dosage. The interval of the administration is varied according to the symptom and, therefore, it is not specifically restricted. For example, the pharmaceutical composition of the present invention may be administered at an interval of several hours to several days.

The anti-cerebral edema activity of the pharmaceutical composition of the present invention was confirmed by the rat cerebral edema testing system using the following two animal models:

(1) the Tamura's experimental model for ischemic cerebral edema, the middle cerebral artery of which model is constricted, and (2) the cold injury model, which is generally used as an experimental model for vasogenic edema caused by the blood-brain barrier insufficiency.

With respect to the above-mentioned animal models and the experimental methods, reference may be made to, for example:

(1) The Tamura's model (Constriction of middle cerebral artery): Tamura, A., Graham D. I., McCulloch, J., et al., "Focal cerebral ischemia in the rat", J. Cereb. Blood Flow & Metab., 1, 53–69(1981);

(2) The cold injury model: Klatzo, I., Piraux, A., Laskowski, E. J., "The relationship between edema, blood-brain barrier and tissue elements in a local brain injury", J. Neuropath. Exp. Neurol., 17, 548–564(1958); and Shoji Naruse et al, "Study on cerebral edema by NMR—Change with the passage of time in $^1$H-relaxation time—", Cerebral Nerve, 33(6), 569–575 1981);

(3) Compilation of Use of Animal Models for the Development of New Drugs, edited by Ryuta Itoh et al. published by R & D Planning, Japan (1985);

(4) Cerebral Ischemia—Fundamentals and Clinic—, edited by Tsukasa Nakagawa, published by Neuron K.K., Japan (1986); and (5) Chemistry Today, extra number 7, Methods in Researches on Prostaglandins (last volume), edited by Shozo Yamamoto et al., published by Tokyo Kagaku Dojin K.K. (1987).

The anti-cerebral edema activity can be evaluated by determining the water content of a brain tissue, since the cerebral edema is defined by "a symptom defined as an excessive accumulation of water in a brain tissue (including the inside and the outside of the brain cells)". The water content of a brain tissue can be directly determined by the dry-wet method.

As is described in the following Examples, by the intravenous administration of the pharmaceutical composition of the present invention, the amount of water in a brain tissue which has been increased due to ischemic cerebral edema and angiopathic (vasogenic) edema is decreased. This shows that the pharmaceutical composition of the present invention is effective for treating and preventing cerebral edema. Further, the active ingredient of the present pharmaceutical composition, namely the peptide of formula (I), is extremely safe as compared to the conventional anti-cerebral edema agents. Therefore, the pharmaceutical composition of the present invention can advantageously be used for the treatment and prevention of cerebral edema.

The present invention will be described in more detail in the following Reference Examples and Examples.

In the following Examples, the peptide of formula (II) and the peptide of formula (III) are referred to simply as "peptide (II)" and "peptide (III)", respectively.

REFERENCE EXAMPLE 1

Synthesis of Peptide (II)

4 g of a protected peptide represented by formula (5):

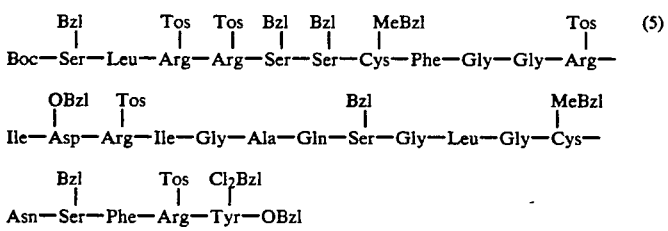

wherein Boc, MeBzl, Tos, $Cl_2Bzl$ and Me are protective groups and have the following meanings: Boc represents a t-butyloxycarbonyl, MeBzl a 4-methylbenzyl, Bzl a benzyl, Tos a tosyl, $Cl_2Bzl$ a 2,6-dichlorobenzyl and Me a methyl, was synthesized by the liquid phase method according to the following reaction steps:

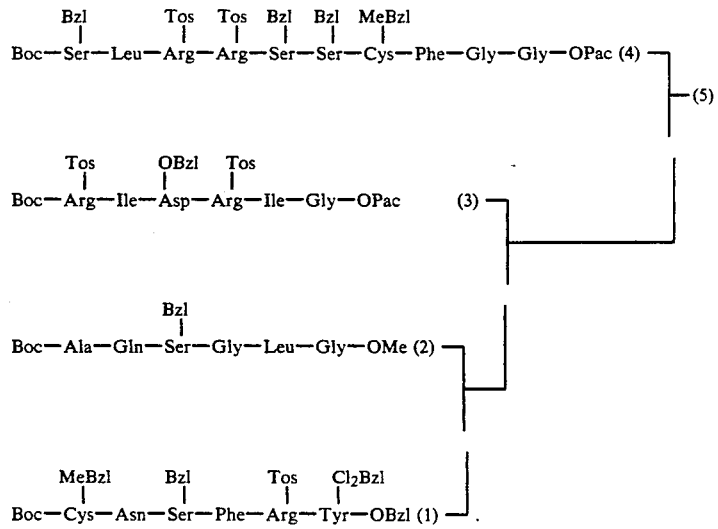

wherein Boc, MeBzl, Tos, $Cl_2Bzl$ and Me have the same meanings as defined above, and Pac is a phenacyl.

Then, 4 g of protected peptide (5) was treated with trifluoroacetic acid ($CF_3COOH$) and further treated with hydrogen fluoride, to thereby remove the protective groups from the peptide. The resultant peptide was subjected to ion exchange chromatography using Dowex 1-X2 resin (manufactured and sold by Dow Chemical Company, U.S.A. to remove the remaining hydrogen fluoride, and then treated with potassium ferricyanide ($K_3Fe(CN)_6$) to form a circular structure by a disulfide bond between two cysteine residues (Cys) present in the molecule. Thus, 3.2 g of crude peptide (II) was obtained. The thus obtained peptide (II) was purified successively by hydrophobic chromatography using Diaion HP-20 (manufactured and sold by Mitsubishi Chemical Industries, Ltd., Japan) and using an aqueous 15% acetonitrile solution as an eluent; ion-exchange chromatography using CM52 resin (manufactured and sold by Whatman Chemical Separation Inc., U.S.A), in which an elution was conducted using as an eluent a 0.05 M ammonium acetate ($NH_4OAc$) containing NaCl while increasing the NaCl concentration from 0.1 M to 0.8 M; hydrophobic chromatography using Diaion HP-20 (manufactured and sold by Mitsubishi Chemical Industries, Ltd., Japan) and using an aqueous solution consisting of 10% methanol, 85% water and 5% acetic acid as an eluent; and gel filtration chromatography using Sephadex G-25 (manufactured and sold by Pharmacia Fine Chemical AB, Sweden) and using an aqueous 5% acetic acid solution as an eluent, to thereby obtain 0.4 g of purified peptide (II). In order to determine the purity of the above-obtained peptide (II), the peptide was subjected to high-performance liquid chromatography (HPLC) under the following conditions.

| Apparatus | LC-6A type HPLC analysis apparatus manufactured and sold by Shimadzu Corp., Japan |
|---|---|
| Column | COSMOSIL Packed Column $5C_{18}$ manufactured and sold by Nakarai Chemical Ltd., Japan |
| Solvent | A) $H_2O$:TFA = 100:0.1<br>B) $CH_3CN$:$H_2O$:TFA = 80:20:0.1 |
| Gradient | Linear gradient of from 25% to 50% of solvent B in solvent A (25 min) |
| Flow rate | 1.0 ml/min |
| Detection | 214 nm |

The purity was determined by calculating the ratio of the area of the peak of the peptide to the total area of the peaks obtained by HPLC. The obtained peptide had a purity of 98.3%.

Further, in order to confirm that the obtained peptide (II) has the intended amino acid sequence, the amino acid sequence of the peptide was analyzed using Protein Sequencer Model 470A (manufactured and sold by Applied Biosystems, Japan) after the peptide was subjected to reductive carboxymethylation of a disulfide bond and Edman degradation. The results are shown in FIGS. 1 and 2.

REFERENCE EXAMPLE 2

Synthesis of Peptide (II)

Peptide (II) was synthesized by the solid phase method using a 4-(hydroxymethyl)-phenylacetoamidemethyl resin (hereinafter referred to as "PAM resin") as a support and using a peptide synthesizer Model 430A (manufactured and sold by Applied Biosystems, Japan) and programs for the peptide synthesizer for bonding various amino acids, which programs are provided by Applied Biosystems, Japan.

Illustratively stated, using 0.5 mmol of Boc-Tyr-(2-Bromobenzyloxycarbonyl)-PAM resin (manufactured and sold by Applied Biosystems, Japan) as a starting material, appropriate protected amino acids manufactured and sold by Applied Biosystems, Japan were successively bonded in sequence according to the above-mentioned amino acid sequence of formula (II), to thereby obtain 2.9 g of a protected peptide-PAM resin.

To 1 g of the thus obtained protected peptide-PAM resin were added 1 ml of thioanisol, 0.5 ml of metacresol, 10 ml of trifluoroacetic acid and 2.3 ml of trimethylsilyltrifluoromethanesulfonate, and the resultant mixture was stirred at 0° C. for 1 hour. By the above-mentioned treatment, the protected peptide was cut off from the PAM resin, and the protective groups were removed from the protected peptide. Then, the mixture was subjected to filtration, to thereby remove the cut-off PAM resin. The filtrate was concentrated under reduced pressure. To the above-concentrated filtrate was added ether to obtain a precipitate, and the precipitate was treated with 1 M ammonium fluoride (pH 8.0) and subjected to filtration and lyophilization, to thereby obtain 0.3 g of crude peptide (II).

Then, the obtained peptide was treated with potassium ferricyanide to form a circular structure by a disulfide bond between two cysteine residues (Cys) present in the molecule. The resultant peptide was applied to a column (4 cm × 10 cm) packed with Diaion HP-20 (manufactured and sold by Mitsubishi Chemical Industries, Ltd., Japan) and washed with water. The peptide adsorbed on the column was eluted out with an aqueous 60% acetonitrile solution, to thereby obtain a fraction containing 0.2 g of a peptide. Then, the thus obtained peptide was subjected to HPLC using a column (COSMOSIL $5C_{18}$, manufactured and sold by Nakarai Chemical Ltd., Japan) to obtain a fraction containing the peptide. Thus, there was obtained 70 mg of peptide (II) having a purity of about 95%.

REFERENCE EXAMPLE 3

Synthesis of Peptide (III)

Peptide of formula (III) was synthesized by the solid phase method using PAM resin as a support and using a peptide synthesizer Model 430A (manufactured and sold by Applied Biosystems, Japan) and programs for the peptide synthesizer for bonding various amino acids, which programs are provided by Applied Biosystems, Japan.

Illustratively stated, using 0.5 mmol of Boc-Tyr-(2-Bromobenzyloxycarbonyl)-PAM resin (manufactured and sold by Applied Biosystems, Japan) as a starting material, appropriate protected amino acids manufactured and sold by Applied Biosystems, Japan were successively bonded in sequence according to the above-mentioned amino acid sequence of formula (III), to thereby obtain 2.5 g of a protected peptide-PAM resin.

To 1 g of the thus obtained protected peptide-PAM resin were added 1 ml of thioanisol, 0.5 ml of metacresol, 10 m of trifluoroacetic acid and 2.3 ml of trimethylsilyltrifluoromethanesulfonate, and the resultant mixture was stirred at 0° C. for 1 hour. By the above-mentioned treatment, the protected peptide was cut off from the PAM resin, and the protective groups were removed from the protected peptide. Then, the mixture was subjected to filtration, to thereby remove the cut-off PAM resin. The filtrate was concentrated under reduced pressure. To the above-concentrated filtrate was added ether to obtain a precipitate, and the precipitate was treated with 1 M ammonium fluoride (pH 8.0) and subjected to filtration and lyophilization, to thereby obtain 0.3 g of crude peptide (III).

Then, in order to reduce the oxidized methionine residue, the obtained peptide was dissolved in 50 ml of water and the solution was adjusted to pH 8.0 with an aqueous 5% ammonium hydroxide solution. To the solution was added 0.8 g of dithiothreitol, and the resultant mixture was incubated at 37° C. for 24 hours. The resultant reaction mixture was applied to a column (4 cm × 10 cm) packed with Diaion HP-20 (manufactured and sold by Mitsubishi Chemical Industries, Ltd., Japan) and washed with water. The peptide adsorbed on the column was eluted out with an aqueous 60% acetonitrile solution, to thereby obtain a fraction containing 0.3 g of a peptide. Then, the thus obtained peptide was treated with potassium ferricyanide to form a circular structure by a disulfide bond between two cysteine residues (Cys) present in the molecule. The resultant reaction mixture was applied to a column (4 cm × 10 cm) packed with Diaion HP-20 (manufactured and sold by Mitsubishi Chemical Industries, ltd., Japan) and washed with water. The peptide adsorbed on the column was eluted out with an aqueous 60% acetonitrile solution, to thereby obtain a fraction containing 0.2 g of a peptide. The thus obtained peptide was subjected to HPLC using a column (COSMOSIL 5C$_{18}$ manufactured and sold by Nakarai Chemical Ltd., Japan) to obtain a fraction containing the peptide. Thus, 30 mg of peptide (III) having a purity of about 95% was obtained.

EXAMPLE 1

Preparation of Pharmaceutical Composition 200 mg of citric anhydride was dissolved in about 8 ml of distilled water for injection. To the solution was added 25 mg of peptide (II) obtained in Reference Example 1. To the resultant solution was added 5 N aqueous sodium hydroxide solution to adjust the pH of the solution at 5.0. Then, distilled water for injection was added to the solution until the total volume of the solution became 10 ml. The resultant solution was sterilized by filtration. The thus obtained solution was distributed into 5 vials in an amount of 2 ml per vial. The solution in each vial was subjected to pre-freezing at −38° C. Then, lyophilization was conducted successively at −39° C. for 3 hours, at −19° C. for 3 hours, at −9° C. for 4 hours, at 25° C. for 7 hours and at 31° C. for 5 hours (the temperature elevation between the respective lyophilization conditions was conducted over 1 hour), under a pressure of 0.7 Torr or lower. After completion of the lyophilization, dry nitrogen gas was introduced into each of the vials until the pressure in the vial became 560 mmHg and each vial was sealed. Thus, there were obtained 5 vials of lyophilized preparations containing peptide (II).

EXAMPLE 2

Preparation of Pharmaceutical Composition 80 mg of citric anhydride was dissolved in about 3 ml of distilled water for injection. To the solution was added 10 mg of peptide (III) obtained in Reference Example 3. To the resultant solution was added 5 N aqueous sodium hydroxide solution to adjust the pH of the solution at 5.0. Then, distilled water for injection was added to the solution until the total volume of the solution became 4 ml. The resultant solution was sterilized by filtration. The thus obtained solution was distributed into 2 vials in an amount of 2 ml per vial. The solution in each vial was subjected to pre-freezing at −40° C. Then, lyophilization was conducted successively at −40° C. for 3 hours, at −20° C. for 3 hours, at −10° C. for 4 hours, at 28° C. for 7 hours and at 30° C. for 7 hours (the temperature elevation between the respective lyophilization conditions was conducted over 1 hour), under a pressure of 0.7 Torr or lower. After completion of the lyophilization, dry nitrogen gas was introduced into each of the vials until the pressure in the vial became 560 mmHg and each vial was sealed. Thus, there were obtained 2 vials of lyophilized preparations containing peptide (III).

EXAMPLE 3

Preparation of Pharmaceutical Composition 140 mg of lactic acid was dissolved in about 8 ml of distilled water for injection. To the solution was added 25 mg of peptide (II) obtained in Reference Example 1. To the resultant solution was added 5N aqueous sodium hydroxide solution to adjust the pH of the solution at 5.0. Then, distilled water for injection was added to the solution until the total volume of the solution became 10 ml. The resultant solution was sterilized by filtration. The thus obtained solution was distributed into 5 vials in an amount of 2 ml per vial. The solution in each vial was subjected to pre-freezing at −40° C. Then, lyophilization was conducted successively at −39° C. for 3 hours, at −20° C. for 3 hours, at −10° C. for 4 hours, at 25° C. for 7 hours and at 31° C. for 7 hours (the temperature elevation between the respective lyophilization conditions was conducted over 1 hour), under a pressure of 0.7 Torr or lower. After completion of the lyophilization, dry nitrogen gas was introduced into each of the vials until the pressure in the vial became 560 mmHg and each vial was sealed. Thus, there were obtained 5 vials of lyophilized preparations containing peptide (II).

EXAMPLE 4

Effect on Experimental Ischemic Cerebral Edema

Using 41 male Wistar rats weighing 250 to 350 g, model animals of ischemic cerebral edema caused by occlusion of middle cerebral artery (hereinafter referred to as "MCA") were prepared according to the method of Tamura et al. (Journal of Cerebral Blood Flow and Metabolism, 1, 53–69 (1981)).

Administration Method

Peptide (II) obtained in Reference Example 1 was diluted with a physiological saline so that the peptide concentration became 100 μg/10 ml. The solution containing the peptide was continuously administered to eleven rats through the tail vein thereof in an amount of 10 ml per kg of body weight in 20 min so that the total dose of the administered peptide became 100 μg per kg of body weight.

The administration was conducted 6 times according to the following program. The first administration was conducted 30 minutes after the occlusion of MCA. The second administration was conducted in the morning of the next day of the first administration (2nd day). The third administration was conducted after 6 hours from the second administration. The fourth administration was conducted in the morning of the next day of the third administration (3rd day). The fifth administration was conducted after 6 hours from the fourth administration and the sixth administration was conducted in the morning of the next day of the fifth administration (4th day). Thus, there was obtained a peptide (II)-administered group.

Peptide (III) was administered to eight rats in the same manner as described above except that peptide (III) was used instead of peptide (II), to thereby obtain a peptide (III)-administered group.

As a control for the peptide, an aqueous 10% w/v glycerol solution containing 5% w/v fructose and 0.9% w/v sodium chloride which is a hyperosmotic agent was administered to eleven rats in substantially the same manner as mentioned above so that the total amount of the administered glycerol became 1 g per kg of body weight, to thereby obtain a glycerol-administered group.

As a control (solvent), 10 ml per kg of body weight of the physiological saline was administered to eleven rats in substantially the same manner as mentioned above, to thereby obtain a physiological saline-administered group.

Measuring Method

After one hour from the sixth administration, that is, 3 days after the rats had been subjected to occlusion of MCA, the rats were sacrificed. Then, cerebra were extracted from the killed rats and each of the cerebra was individually divided into two cerebral hemispheres, namely, a hemisphere having ischemic part and a hemisphere having no ischemic part. The water content of each of the hemispheres was measured.

The water content of a brain tissue was calculated by the following formula:

$$\text{Water content of a brain tissue (\%)} = \frac{W_1 - W_2}{W_1} \times 100$$

wherein:

$W_1$: weight of the cerebral hemisphere (wet basis)
$W_2$ weight of the cerebral hemisphere (dry basis), which is measured after drying the wet cerebral hemisphere at 95° to 100° C. for 3 days.

The water contents calculated were statistically analyzed by the T-test to determine whether or not there is a significant difference between the water content of each of the groups to which peptide (II), peptide (III) and glycerol were individually administered and the water content of the control group to which physiological saline was administered.

The results are shown in Table 1. In Table 1, the mean and the standard error of the water content of a brain tissue are shown together with the number of rats (n) subjected to experiment in each group.

TABLE 1

| Test sample | Water content of brain tissue (the mean ± standard error) | |
|---|---|---|
| | Hemisphere having ischemic part | Hemisphere having no ischemic part |
| Peptide (II) | 79.34 ± 0.15* (n = 11) | 78.51 ± 0.15 (n = 11) |
| Peptide (III) | 79.40 ± 0.13* (n = 8) | 78.56 ± 0.14 (n = 8) |
| Glycerol | 79.34 ± 0.15* (n = 11) | 78.51 ± 0.14 (n = 11) |
| Physiological saline | 79.95 ± 0.19 (n = 11) | 78.93 ± 0.1 (n = 11) |

Note: *level of significance is 5% (P < 0.05).

With respect to the peptide (II)-administered group, peptide (III)-administered group and glycerol-administered group, an increase in water content of the cerebral hemisphere having ischemic part was significantly inhibited (P 0.05) as compared to that of the cerebral hemisphere having ischemic part with respect to the physiological saline-administered group.

EXAMPLE 5

Effect on Experimental Vasogenic Cerebral Edema

Using 42 male Crj:CD (SD) rats weighing 300 to 400 g, model animals of vasogenic cerebral edema caused by cold injury were prepared according to the method of Naruse et al. (Brain and Nerve, 33 (6): 569-575 (1981)). (Administration method)

Peptide (II) obtained in Reference Example 1 was diluted with a physiological saline so that the peptide concentration became 100 μg/3 ml. The solution containing the peptide was continuously administered to eleven rats through the tail vein thereof in an amount of 10 ml per kg of body weight so that the total dose of the administered peptide became 100 μg per kg of body weight, to thereby obtain a peptide (II)-administered group.

Peptide (III) was administered to eight rats in the same manner as described above except that peptide (III) was used instead of peptide (II), to thereby obtain a peptide (III)-administered group.

As a control (solvent), 3 ml per kg of body weight of the physiological saline was administered to eleven rats in substantially the same manner as mentioned above, to thereby obtain a physiological saline-administered group.

As a control for the peptide, an aqueous 10% w/v glycerol solution containing 5% w/v fructose and 0.9% w/v sodium chloride was administered to twelve rats so that the total volume of the administered solution became 10 ml per kg of body weight, to thereby obtain a glycerol-administered group.

The administration of each of the peptide (II) solution, peptide (III) solution and physiological saline was started one hour before the making of cold injury and completed in 90 minutes. On the other hand, the administration of the glycerol solution was started 23 hours after the making of cold injury and completed in 30 minutes in accordance with the ordinary clinical method, so that the total volume of the administered glycerol solution became 10 ml/kg of body weight.

Measuring Method 24 hours after the rats had been subjected to cold injury, rats were sacrificed under ether anesthesia. Then, cerebra were extracted from the killed rats and each of the cerebra was individually divided into two cerebral hemispheres, namely, a hemisphere having ischemic part and a hemisphere having no ischemic part.

The water content of each of the hemispheres was measured in substantially the same manner as in Example 1. The results are shown in Table 2. In Table 2, the mean and the standard error of the water content of a brain tissue are shown together with the number of rats (n) subjected to experiment in each group.

TABLE 2

| Test sample | Water content of brain tissue (the mean ± standard error) | |
|---|---|---|
| | Injured cerebral hemisphere | Not injured cerebral hemisphere |
| Peptide (II) | 80.44 ± 0.09** (n = 11) | 79.59 ± 0.08 (n = 11) |
| Peptide (III) | 80.50 ± 0.15* (n = 8) | 79.60 ± 0.11 (n = 8) |
| Glycerol | 80.65 ± 0.23 (n = 12) | 79.62 ± 0.19 (n = 12) |
| Physiological saline | 80.96 ± 0.13 (n = 11) | 79.89 ± 0.08 (n = 11) |

Note:
*level of significance is 5% (P < 0.05).
**level of significance is 1% (P < 0.01).

With respect to the peptide (II) administered-group and the peptide (III) administered-group, an increase in water content of the injured cerebral hemisphere was markedly inhibited (P<0.01 and P<0.05) as compared to that of the injured cerebral hemisphere with respect to the physiological saline-administered group. On the other hand, in the glycerol-administered group, an increase in water content of the injured cerebral hemisphere was not so markedly inhibited as compared to that with respect to the physiological saline-administered group.

EXAMPLE 6

Effect on Experimental Vasogenic Cerebral Edema (Investigation of Administration Time)

Using 212 male Crj:CD (SD) rats weighing 300 to 400 g, model animals of vasogenic cerebral edema caused by cold injury were prepared according to the method of Naruse et al. (Brain and Nerve, 33 (6): 569–575 (1981).

Administration Method

Peptide (II) obtained in Reference Example 1 was diluted with a physiological saline so that the peptide concentration became 100 µg/3 ml. The solution containing the peptide was continuously administered to a predetermined number of rats through the tail vein thereof in an amount of 3 ml per kg of body weight in 90 min so that the total dose of the administered peptide became 100 µg per kg of body weight. The time of the initiation of the administration was changed as shown in Table 3. Thus, there were obtained six peptide (II)-administered groups.

As a control (solvent), 3 ml per kg of body, weight of the physiological saline was administered to a predetermined number of rats in substantially the same manner as mentioned above, to thereby obtain six physiological saline-administered groups.

As a control for the peptide, an aqueous 10% w/v glycerol solution containing 5% w/v fructose and 0.9% w/v sodium chloride was administered to a predetermined number of rats in substantially the same manner as mentioned above so that the total volume of the administered solution became 10 ml per kg of body weight, to thereby obtain six glycerol-administered groups.

Measuring Method 24 hours after the rats were subjected to injury, rats were exsanguinated under ether anesthesia to kill them. Then, cerebra were extracted from the killed rats and each of the cerebra was individually divided into two cerebral hemispheres, namely, a hemisphere having ischemic part and a hemisphere having no ischemic part. The water content of each of the hemispheres was measured in substantially the same manner as in Example 1. The results are shown in Table 3. In Table 3, the mean and the standard error of the water content of a brain tissue are shown together with the number of rats (n) subjected to experiment in each group.

TABLE 3

| Administration time | Water content of injured cerebral hemisphere (the mean ± standard error) | | |
|---|---|---|---|
| | Peptide (II) | Physiological saline | Glycerol |
| Just before the making of cold injury | 80.78 ± 0.12* (n = 12) | 81.16 ± 0.09 (n = 12) | 81.22 ± 0.20 (n = 12) |
| During the making of cold injury | 80.44 ± 0.09** (n = 11) | 80.96 ± 0.13 (n = 11) | 80.79 ± 0.10 (n = 7) |
| Just after the making of cold injury | 80.76 ± 0.07** (n = 12) | 81.18 ± 0.12 (n = 12) | 80.77 ± 0.14* (n = 12) |
| 3 hours after the making of cold injury | 80.49 ± 0.18* (n = 10) | 81.11 ± 0.16 (n = 10) | 81.08 ± 0.20 (n = 14) |
| 6 hours after the making of cold injury | 80.85 ± 0.13 (n = 9) | 80.85 ± 0.13 (n = 17) | 81.24 ± 0.19 (n = 6) |
| 22 hours after the making of cold injury | 80.66 ± 0.17 (n = 15) | 80.93 ± 0.13 (n = 18) | 81.05 ± 0.17 (n = 12) |

Note:
*level of significance is 5% ($P < 0.05$).
**level of significance is 1% ($P < 0.01$).

With respect to the peptide (II)-administered groups, when peptide (II) was administered just before, during, just after or three hours after the making of cold injury, an increase in water content of the injured cerebral hemisphere was significantly inhibited as compared to that of the injured cerebral hemisphere with respect to the physiological saline-administered groups. However, when peptide (II) was administered 6 hours and 22 hours after the making of cold injury, an increase in water content of a cerebral hemisphere was not significantly inhibited.

On the other hand, in the glycerol-administered groups, only with respect to the group to which glycerol was administered just after making the cold injury, an increase in water content of a cerebral hemisphere was significantly inhibited as compared to that with respect to the physiological saline-administered groups. However, an increase in water content of the injured cerebral hemisphere was not significantly inhibited with respect to the remaining glycerol-administered groups.

As is apparent from the results described above, the administrations of peptide (II) before and after the making of cold injury, respectively, were effective for relieving the symptom of cerebral edema. It is also apparent that peptide (II) exhibits anti-cerebral edema activity more effectively when it is administered as soon as possible after the making of cold injury.

EXAMPLE 7

Acute Toxicity Study (1) Acute toxicity in rats

1) Test drug

Peptide (II) having a purity of 98.3% which was obtained in Reference Example 1 was dissolved in a physiological saline to prepare three preparations having peptide (II) concentrations of 0.1 mg/ml, 0.3 mg/ml and 1.0 mg/ml, respectively. As a control, the physiological saline was used.

2) Test animal and group construction

88 Crj:CD (SD) rats of 4 weeks old (including 44 male rats and 44 female rats) were purchased from Charles River Japan, Inc., Japan. 40 Rats of each sex (males weighing 116.3 to 138.0 g and females 114.4 to 130.2 g) which were healthy and in good conditions in respect of both the clinical signs and the body weight gain during the observation period for quarantine and acclimation (male: 6 days, female: 8 days) were selected from the purchased rats and used for the following experiment. The rats were divided at random into four groups each consisting of 10 male rats and 10 female rats. Three of the four groups are used for the treatment with peptide (II).

3) Dosage levels and administration method

Each of the above-prepared three test drug solutions containing peptide (II) at concentrations of 0.1 mg/ml, 0.3 mg/ml and 1.0 mg/ml, respectively, was individually administered at one time to the rats of the three groups at a dosage of 5 ml/kg of body weight. That is, the peptide was administered to the rats of the three groups at dosages of 0.5 mg/kg, 1.5 mg/kg and 5.0 mg/kg of body weight, respectively. To the rats of the remaining group, physiological saline was administered as a control at a dosage of 5 ml/kg of body weight. The administration of each of the test drug solutions and the physiological saline was conducted through the tail vein of each rat at an administration rate of 1 ml/min.

4) Observation, measurements and examinations (i) Observation of clinical signs

The animals were observed to examine whether or not the death of rats and/or any remarkable changes in clinical signs had occurred, every hour until 6 hours after the administration and then twice a day during the two-week observation period. The results were recorded.

(ii) Measurement of food consumption

The amounts of the food supplied and the food remaining were measured twice a week by means of a balance, and the food consumption per day per animal was calculated.

(iii) Measurement of body weight

The body weight of each animal was measured three times a week.

(iv) Patho-anatomical examination

The animals were exsanguinated under ether anesthesia on the next day of the two-week observation period. Then, various organs and tissues of the animals were observed by gross autopsy.

5) Examination results

The results are shown in Table 4.

TABLE 4

| | Examination results |
|---|---|
| Clinical signs | No dead animal |
| | No remarkable change |
| Food consumption | No remarkable change |
| Change in body weight | No remarkable change |
| Patho-anatomical examination | No remarkable change |

(2) Acute toxicity in cynomolgus monkeys

1) Test drug

Peptide (II) having a purity of 98.3% which was obtained in Reference Example 1 was dissolved in a physiological saline to prepare three preparations 1, having peptide (II) concentrations of 0.1 mg/ml, 0.3 mg/ml and 1.0 mg/ml, respectively. As a control, the physiological saline was used.

2) Test animal and group construction

Approximately 3 to 6 year-old cynomolgus monkeys of both sexes were purchased from American Charles River Research Primates, Ltd., U.S.A. The animals were bred for approximately 6 months and then observed one week during quarantine and acclimation. From the purchased monkeys, 6 male monkeys and 6 female monkeys (males weighing 2.31 to 4.22 kg and females weighing 2.45 to 2.66 kg) which were healthy and in good condition in respect of both the clinical signs and the body weight gain were selected from the purchased monkeys and used for the following experiment.

The selected monkeys were divided at random into three groups each consisting of two males and two females.

3) Dosage levels and administration method

Each of the above-prepared three test drug solutions containing peptide (II) at concentrations of 0.1 mg/ml, 0.3 mg/ml and 1.0 mg/ml, respectively, was individually administered at one time to the monkeys of the three groups at a dosage of 5 ml/kg of body weight. That is, the peptide was administered to the monkeys of the three groups at dosages of 0.5 mg/kg, 1.5 mg/kg and 5.0 mg/kg of body weight, respectively. To the monkeys of the remaining group, physiological saline was administered as a control at a dosage of 5 ml/kg of body weight. The administration of each of the test drug solutions and the physiological saline was conducted through the median antebrachial vein of each monkey at an administration rate of 10 ml/min.

4) Observations, measurements and examinations (i) Observation of clinical signs The animals were observed to examine whether or not the death of monkeys and/or any remarkable changes in clinical signs had occurred, every hour until 6 hours after the administration and then twice a day during the two-week observation period, and the observations were recorded.

(ii) Measurement of food consumption

The amounts of the food supplied and the food remaining were measured daily by means of a balance, and the food consumption per animal was calculated.

(iii) Measurement of body weight

The body weight of each animal was measured by means of a balance at a time between 2 p.m. and 4 p.m. daily.

(iv) Patho-anatomical examination

The animals were exsanguinated under sodium pentobarbital anesthesia on the day after the two-week observation period. Then, various organs and tissues of the animals were observed by gross autopsy.

(v) Measurement of organ weight

The weights of various organs of the animals were measured by means of an electronic balance.

5) Examination results

The results obtained are shown in Table 5.

TABLE 5

| | Examination results |
|---|---|
| Clinical signs | No dead animal |
| | No remarkable change |
| Food consumption | No remarkable change |
| Change in body weight | No remarkable change |
| Patho-anatomical examination | No remarkable change |
| Organ weight | No remarkable change |

EXAMPLE 8

14-Day Toxicity by Intravenous Administration (1) 14-day toxicity in rats by intravenous administration 1) Test drug Peptide (II) having a purity of 98.3% which was obtained in Reference Example 1 was dissolved in a physiological saline to prepare three preparations having the peptide (II) concentrations of 0.025 mg/ml, 0.075 mg/ml and 0.25 mg/ml, respectively. As a control, the physiological saline was used.

2) Test animal and group construction

100 Crj:CD (SD) SPF rats of 4 weeks old of both sexes (50 male rats and 50 female rats) were purchased from Charles River Japan, Inc., Japan. 40 Rats of each sex (males weighing 102.4 to 114.6 g and females weighing 92.9 to 104.2 g) which were healthy and in good conditions in respect of both the clinical signs and the body weight gain during about one-week observation period for the quarantine and the acclimation were selected and used for the following experiment.

The rats were divided at random into four groups each consisting of 10 male rats and 10 female rats. Three of the four groups are used for the treatment with peptide (II).

3) Dosage levels and administration method

Each of the above-prepared three test drug solutions containing peptide (II) at concentrations of 0.025 mg/ml, 0.075 mg/ml and 0.25 mg/ml, respectively, was individually administered to the rats of the three groups at a dosage of 0.2 ml/100 g of body weight. That is, the peptide was administered to the rats of the three groups at dosages of 0.05 mg/kg, 0.15 mg/kg and 0.5 mg/kg of body weight, respectively. To the rats of the remaining group, physiological saline was administered as a control at a dosage of 0.2 ml/100 g of body weight. The administration of each of the test drug solutions and the physiological saline was conducted daily for 14 days through the tail vein of each rat (with the weekly alteration between the left side and right side tail veins) at an administration rate of 0.5 ml/sec (once a day at a time between 1:00 p.m. and 3:00 p.m.).

4) Observation, measurements and examinations (i) Observation of clinical signs

Each rat was observed 4 times a day to examine whether or not it was dead and/or any remarkable changes in clinical signs had occurred. The results were recorded.

(ii) Measurement of food consumption

The amounts of the food supplied and the food remaining were measured by means of a balance twice a week during the administration period, and the daily food consumption per animal was calculated.

(iii) Measurement of water consumption

The amount of water consumption was measured once a week during the administration period.

(iv) Measurement of body weight

The individual body weight was measured on the first day of the administration and then twice a week during the administration period.

(v) Ophthalmic examination

Each of the male and female rats of the control group and the highest dosage group (0.5 mg/kg of body weight) were subjected to examination of bilateral fundus oculi on the 11th administration day.

(vi) Hematological examination

Samples of abdominal aorta blood were obtained from all of the rats on the day after the 14th administration day under ether anesthesia. One ml of each blood sample was transferred to an EDTA 2K tube (manufactured and sold by Toa Medical Electronics Co., Japan) and examined with respect to the following parameters using an automatic blood cell counter CC-108 (manufactured and sold by Toa Medical Electronics Co., Japan), automatic platelet counter PL-100 (manufactured and sold by Toa Medical Electronics Co., Japan) and automatic hemoglobinmeter HB-100 (manufactured and sold by Toa Medical Electronics Co., Japan): TE-400 (manufactured and sold by Erma Optical Works Ltd., Japan):

Parameters

Erythrocyte count (RBC),
Leukocyte count (WBC),
Hemoglobin content (Hb),
Hematocrit value (Ht),
Platelet count,
Reticulocyte ratio,
Differential leukocyte count,
Mean corpuscular volume (MCV),
Mean corpuscular hemoglobin (MCH), and
Mean corpuscular hemoglobin concentration (MCHC).

(vii) Blood biological examination

Samples of abdominal aorta blood were obtained from all of the rats on the day after the 14th administration day under ether anesthesia. An aliquot (one ml) of each blood sample was immediately transferred to a heparin-coated tube. Within ten minutes, the samples were centrifuged at 1000G at 4° C. for two minutes and the plasma was separated for analyses of lactate dehydrogenase, sodium, potassium and chloride. On the other hand, another aliquot (ten ml) of each blood sample was centrifuged at 1350G at 4° C. for 10 minutes after keeping it stand still for 15 to 90 minutes, to thereby obtain serum. Each serum was separated for analyses of the other parameters shown below. The following parameters were measured using Centrifi-Chem Encore (manufactured and sold by Baker Instr. Inc.), Na, K and Cl-analyzer IT-3 (manufactured and sold by JOKOO Co., Japan), electrophoresis method (manufactured and sold by JOKOO Co., Japan) and DENSITRON ® 20M-3 (manufactured and sold by JOKOO Co., Japan).

Parameters

Glutamic-oxaloacetic transaminase (GOT),
Glutamic-pyruvic transaminase (GPT),
Alkaline phosphatase (AlP),
Lactose dehydrogenase (LDH),
Glucose (Glu),
Triglyceride (TG),
Total cholesterol (TC),
Free cholesterol (FC),
Phospholipid (PL),
Total bilirubin (T.Bi)
Blood urea nitrogen (BUN),
Creatinine (Crea),
Iron (Fe),
Calcium (Ca),
Inorganic phosphorus (IP), Total protein (TP),
Sodium (Na),
Potassium (K),
Chloride (Cl),
Ratio of albumin to globulin (A/G ratio),
Albumin (Alb), and
Globulin (Glob).

(viii) Urinalysis

A total amount of urine for whole day was daily collected from each of the male rats as from the first to the 12th or 13th administration day, and from each of the female rats as from the first to the 13th or 14th administration day, and the volume of each of the collected urine samples was measured to determine the change in 24-hour urine volume.

(ix) Measurement of organ weight

The weights of various organs of the animals were measured by means of an electronic balance.

(x) Patho-anatomical examination

The animals were exsanguinated on the day after the 14th administration day under ether anesthesia. Then, various organs and tissues of the animals were observed by gross autopsy.

(xi) Histopathological examination

Various organs and tissues of the animals were fixed in 10% buffered neutral formalin. After the fixation, haematoxylin and eosin-stained paraffin sections were prepared from the fixed organs and tissues and observed by means of an optical microscope.

5) Examination results

The results are shown in Table 6.

TABLE 6

| | Examination results |
|---|---|
| Clinical signs | No dead animal |
| | No remarkable change |
| Food consumption | No remarkable change |
| Water consumption | No remarkable change |
| Change in body weight | No remarkable change |
| Ophthalmic examination | No remarkable change |
| Hematological examination | No remarkable change |
| Blood biochemical examination | No remarkable change |
| Urinalysis | No remarkable change |
| Measurement of organ weight | No remarkable change |
| Patho-anatomical examination | No remarkable change |
| Histopathological examination | No remarkable change |

(2) Subacute Toxicity in Cynomolgus Monkeys by Intravenous Administrations for Two Weeks and Two-Week Recovery Test 1) Test drug Peptide (II) having a purity of 98.3% which was obtained in Reference Example 1 was dissolved in a physiological saline to prepare two preparations having peptide (II) concentrations of 0.03 mg/ml and 0.1 mg/ml, respectively. As a control, the physiological saline was used.

2) Test animal and group construction

Approximately 3 to 6 year-old cynomolgus monkeys of both sexes were purchased from American Charles River Research Primates Ltd., U.S.A. The animals were bred for approximately 6 months and then observed two weeks for the quarantine and the acclimation. From the purchased monkeys, 10 male monkeys (weighing 2.15 to 3.03 kg) and 10 female monkeys (weighing 2.23 to 2.53 kg) which were healthy and in good conditions in respect of both the clinical signs and the body weight gain during the two-week observation period were selected from the purchased monkeys and used for the following experiment.

10 Males and 10 females were divided at random into three groups, namely, a first group to which peptide (II) is to be administered at a dosage of 5 mg/kg of body weight (4 males and 4 females), a second group to which peptide (II) is to be administered at a dosage of 1.5 mg/kg of body weight (2 males and 2 females) and a third group (control) to which physiological saline is to be administered (4 males and 4 females). With respect to the first group and the third group, 2 males and 2 females of each group were subjected to recovery testing after the administration.

3) Dosage levels and administration method

Each of the above-prepared two test drug solutions containing peptide (II) at concentrations of 0.03 mg/ml and 0.1 mg/ml, respectively, was individually administered to the monkeys of the two groups at a dosage of 5 ml/kg of body weight. That is, the peptide was administered to the monkeys of the two groups at dosages of 0.15 mg/kg and 0.5 mg/kg of body weight, respectively. To the monkeys of the remaining group, physiological saline was administered as a control at a dosage of 5 ml/kg of body weight. The administration of each of the test drug solutions and the physiological saline was conducted daily for 14 days through the median antebrachial vein of each monkey at an administration rate of 10 ml/min.

4) Observation, measurements and examinations (i) Observation of clinical signs

The animals were daily observed to examine whether or not any of the animals was dead and/or any remarkable change in clinical signs had occurred. The observed results were recorded.

ii) Measurement of food consumption

The amounts of the food supplied and the food remaining were daily measured by means of a balance, and the daily food consumption per animal was calculated.

(iii) Measurement of body weight

The individual body weight was daily measured at a time between 2:00 p.m. to 4:00 p.m. by means of a balance.

(iv) Ophthalmic examination

The external appearance of the animals was observed daily by naked eye. Further, the examination of the bilateral fundus oculi was carried out prior to the administration, two weeks after the administration and two weeks after the withdrawal of the administration.

(v) Electrocardiogram examination

The electrocardiogram examination was carried out two weeks before the administration, two weeks after the administration and two weeks after withdrawal of the administration.

(vi) Urinalysis

The urine was collected from each monkey for 18 hours two weeks before the administration, two weeks after the administration and two weeks after withdrawal of the administration, and the volume thereof was measured.

(vii) Hematology

The hematological examination was carried out in the same manner as described above two weeks before the administration, two weeks after the administration and two weeks after the withdrawal of the administration.

(viii) Blood biochemical examination

The blood biochemical examination was carried out in the same manner as described above two weeks before the administration, two weeks after the administration and two weeks before the withdrawal of the administration.

(ix) Patho-anatomical examination

The animals were exsanguinated under sodium pentobarbial anesthesia on the day after the 14th administration period in the case of the monkeys for acute toxicity test and after the administration withdrawal period in the case of the monkeys for the recovery test. Various organs and tissues of each monkey were observed by gross autopsy.

(x) Organ weight

The weight of various organs were measured by means of an electronic balance.

(xi) Histopathological examination

Various organs and tissues of each of the male and female monkeys in the control group and in the highest dosage (0.5 mg/kg) administration group were fixed in 10% buffered neutral formalin. After the fixation, thin sectioned specimens were prepared by a standard method and observed by means of an optical microscope.

5) Examination results

The results are shown in Table 7.

TABLE 7

|  | Examination results |
| --- | --- |
| Clinical signs | No dead animal |
|  | No remarkable change |
| Food consumption | No remarkable change |
| Change in body weight | No remarkable change |
| Ophthalmic examination | No remarkable change |

TABLE 7-continued

|  | Examination results |
| --- | --- |
| Electrocardiogram examination | No remarkable change |
| Urinalysis | No remarkable change |
| Hematological examination | No remarkable change |
| Blood biochemical examination | No remarkable change |
| Patho-anatomical examination | No remarkable change |
| Measurement of organ weight | No remarkable change |
| Histopathological examination | No remarkable change |

What is claimed is:

1. A method for treating cerebral edema, which comprises administering toa patient having cerebral edema an effective anti-cerebral edema amount of at least one peptide represented by formula (I):

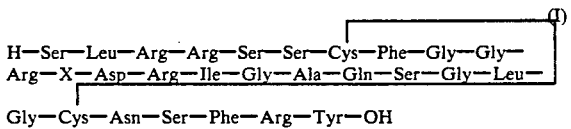

wherein X is an isoleucine residue or a methionine residue.

2. The method according to claim 1, wherein said peptide is in the form of a pharmaceutical composition.

3. The method according to claim 2, wherein said peptide is one represented by formula (I), wherein X is an isoleucine residue.

4. The method according to claim 2, wherein said peptide is one represented by formula (I), wherein X is a methionine residue.

5. The method of claim 1, wherein the effective amount of said at least one peptide is from 0.1 µg to 10 mg per kilogram of a patient's weight.

6. The method of claim 1, wherein the effective amount of said at least one peptide is from 1 µg to 1 mg per kilogram of a patient's weight.

7. The method of claim 1, wherein said peptide is administered intravenously, intramuscularly or subcutaneously.

* * * * *